United States Patent
Flora et al.

(10) Patent No.: US 10,988,705 B2
(45) Date of Patent: Apr. 27, 2021

(54) REMEDIATION OF PESTICIDES FROM AGRICULTURAL OILS

(71) Applicant: APTIA ENGINEERING LLC, Gresham, OR (US)

(72) Inventors: Shale Martin Flora, Gresham, OR (US); Daniel Norman Shelton, Gresham, OR (US); Charles Francavilla, Gresham, OR (US)

(73) Assignee: APTIA ENGINEERING LLC, Gresham, OR (US)

( * ) Notice: Subject to any disclaimer, the term of this patent is extended or adjusted under 35 U.S.C. 154(b) by 0 days.

(21) Appl. No.: 16/809,895

(22) Filed: Mar. 5, 2020

(65) Prior Publication Data
US 2020/0291324 A1    Sep. 17, 2020

Related U.S. Application Data

(60) Provisional application No. 62/817,333, filed on Mar. 12, 2019.

(51) Int. Cl.
*C11B 3/00*       (2006.01)
*B01J 19/00*      (2006.01)
(Continued)

(52) U.S. Cl.
CPC ............ *C11B 3/001* (2013.01); *B01D 15/325* (2013.01); *B01J 19/002* (2013.01);
(Continued)

(58) Field of Classification Search
CPC . C11B 3/001; C11B 3/02; C11B 3/006; C07C 37/68; C07C 37/82; B01D 15/325; B01J 2219/00051
See application file for complete search history.

(56) References Cited

U.S. PATENT DOCUMENTS

| 3,640,821 A | 2/1972 | Sweeny et al. |
| 5,490,919 A | 2/1996 | Pri-Bar et al. |

(Continued)

FOREIGN PATENT DOCUMENTS

| CN | 07027903 a | 8/2017 |
| JP | 2016123330 A | 7/2016 |

(Continued)

OTHER PUBLICATIONS

Fukazawa, et al., "Behavior of 11 Organonitrogen Pesticides during the Refinement of Edible Oils," J. Oleo Science, vol. 54, No. 8, 431-435 (2005), English Abstract Only.
(Continued)

*Primary Examiner* — Yate' K Cutliff
(74) *Attorney, Agent, or Firm* — Miller Nash Graham & Dunn LLP

(57) ABSTRACT

A method of remediating pesticides from an agricultural oil includes mixing a reaction solvent, a reducing agent, and an agricultural oil into a reaction mixture in a reaction vessel, controlling the temperature of the reaction mixture, producing a pre-neutralization mixture including a separation solvent, transferring the pre-neutralization mixture into a neutralization reactor that contains a neutralization agent, mixing the pre-neutralization mixture with the neutralization agent and allowing separation into an aqueous layer and a separation solvent layer, draining the aqueous layer, and distilling the separation solvent in the separation solvent layer from the remediated agricultural oils. A system has a reactor vessel, the reactor vessel having one or more inlets to allow a reducing agent, the agricultural oil, the separation solvent, and other additives as needed to produce a reaction mixture, a temperature control unit to control a temperature of the reaction mixture at a predetermined temperature for a predetermined time, a neutralization vessel fluidically con-
(Continued)

nected to the reactor vessel to receive the reaction mixture from the reactor vessel, the neutralization vessel having an inlet to allow a neutralization agent to be introduced into the neutralization vessel to produce a neutralized reaction mixture, and a valve arranged at a bottom of the neutralization vessel to allow an aqueous phase of the reaction mixture to be drained from the neutralization vessel.

20 Claims, 3 Drawing Sheets

(51) Int. Cl.
  B01D 15/32  (2006.01)
  C11B 3/02   (2006.01)
  C11B 3/12   (2006.01)
  C07C 37/68  (2006.01)
  C07C 37/82  (2006.01)

(52) U.S. Cl.
  CPC .... B01J 19/0053 (2013.01); B01J 2219/0004 (2013.01); B01J 2219/00051 (2013.01); C07C 37/68 (2013.01); C07C 37/82 (2013.01); C11B 3/006 (2013.01); C11B 3/02 (2013.01); C11B 3/12 (2013.01)

(56) References Cited

U.S. PATENT DOCUMENTS

| | | | |
|---|---|---|---|
| 5,558,893 A * | 9/1996 | Muraldihara | C11B 9/022 426/286 |
| 2006/0286134 A1 | 12/2006 | Olansky et al. | |
| 2019/0099697 A1* | 4/2019 | Sibal | B01D 1/222 |

FOREIGN PATENT DOCUMENTS

| | | |
|---|---|---|
| SU | 312090 A1 | 5/1987 |
| WO | 98010046 A1 | 3/1998 |
| WO | 2010055864 A1 | 5/2010 |

OTHER PUBLICATIONS

Al-Taher, et al., "Reduction of Pesticide Residues in Tomatoes and Other Produce," J. Food Protection, vol. 76, No. 3, 510-515 (2013).
Butler, et al. "Reductive Degradation of Dieldrin and Endrin in the Field Using Acidified Zinc," Marcel Dekker, Inc., Environmental Science Health, B16(4), 395-408 (1981).
Honeycutt, et al., "Chemical Treatment Options for Pesticide Wastes Disposal," Product Neutralization Task Force, CIBA-Geigy Corporation, Greensboro, NC, USA, Mar. 17, 2019.
Pittman and He, Dechlorination of PCBs, CAHs, herbicides and pesticides neat and in soils at 25 degrees C using Na/NH3, J. Hazardous Materials, vol. 92, 51-62 (2002).
Ghauch, et al., "Reductive degradation of carbaryl in water by Zero-valent iron," Chemosphere, vol. 41, 419-424 (2001).
Mikesell and Boyd, "Reductive Dechlorination of the Pesticides 2, 4-D, 2, 4, 5-T, and Pentachlorophenol in Anaerobic Sludges," J. Environment Quality, vol. 14, No. 3, 337-340 (1985).
Antonopoulos, et al., "Olive oil and pomace olive oil processing," Grasas Y Aceites, vol. 57(1), Enero-Marzo, 56-67 (2006).
Liu, et al., "The Fate of Organophosphorus Pesticdes during Camellia Oil Production," J. Food Science, vol. 80, Nr. 8, T1926-T1932 (2015).
Bajwa and Sandhu, "Effect of handling and processing on pesticide residues in food—a review," J. Food Science Technology, vol. 51, No. 2, 201-220 (Feb. 2014.
Nikolic, et al., "Pesticides in essential oils and selected fragrance extracts. Some examples. A review.," Flavour Fragrance Journal, vol. 33, 373-384 (2018).
Zhou, Leo, "Removing Pesticides form Cannabis Concentrates," Terpenes and Testing Magazine, online, found at https://terpenesandtesting.com/cannabis-concentrates-pesticides/ printed Mar. 16, 2019.
International Search Report and Written Opinion, PCT/US2020/021097, dated Jul. 16, 2020.
Miyahara et al., "Pesticide removal of soybean oil refining processes," J. Agricultural and Food Chemistry, 1993 41(5), pp. 731-734.

* cited by examiner

REMEDIATION OF PESTICIDES FROM AGRICULTURAL OILS

RELATED APPLICATIONS

This application claims priority to U.S. Provisional Patent Application 62/817,333, filed 12 Mar. 2018, which is incorporated by reference herein in its entirety.

BACKGROUND

Agricultural pesticides can harm humans and/or animals because of the manner in which the pesticides interact with certain neurotransmitters or other biological components within the organism. Often, the mechanism of action that enables the pesticides to kill pests is conserved or similar in higher organisms and therefor can cause problems for humans and other animals.

Little research exists on the acute or chronic effects of inhaling synthetic or naturally occurring agricultural pesticides on humans. As a result, regulators in the majority of states and countries where marijuana or hemp has been legalized for medical and/or recreational use have implemented stringent product quality testing procedures and market restrictions that prevent the sale and consumption of products contaminated with agricultural pesticides. All finished products must undergo analysis at third-party laboratories that test for the presence and concentration of pesticide contaminants using LCMS/MS (liquid chromatography with tandem mass spectrometry) and GCMS/MS (gas chromatography with tandem mass spectrometry). The concentration of pesticides in a given product is quantified to levels well below 0.1 PPM (parts per million) in the majority of states and countries.

For example, Canada, Oregon and California have all implemented very stringent limits on the concentration of agriculture pesticides allowed in finished consumable products. The list of prohibited pesticides is very broad and the permitted limits are in the range of 0.1 PPM. These stringent limits and broad prohibition are more limiting than comparable standards in other industries.

DETAILED DESCRIPTION OF THE EMBODIMENTS

Figure 1:
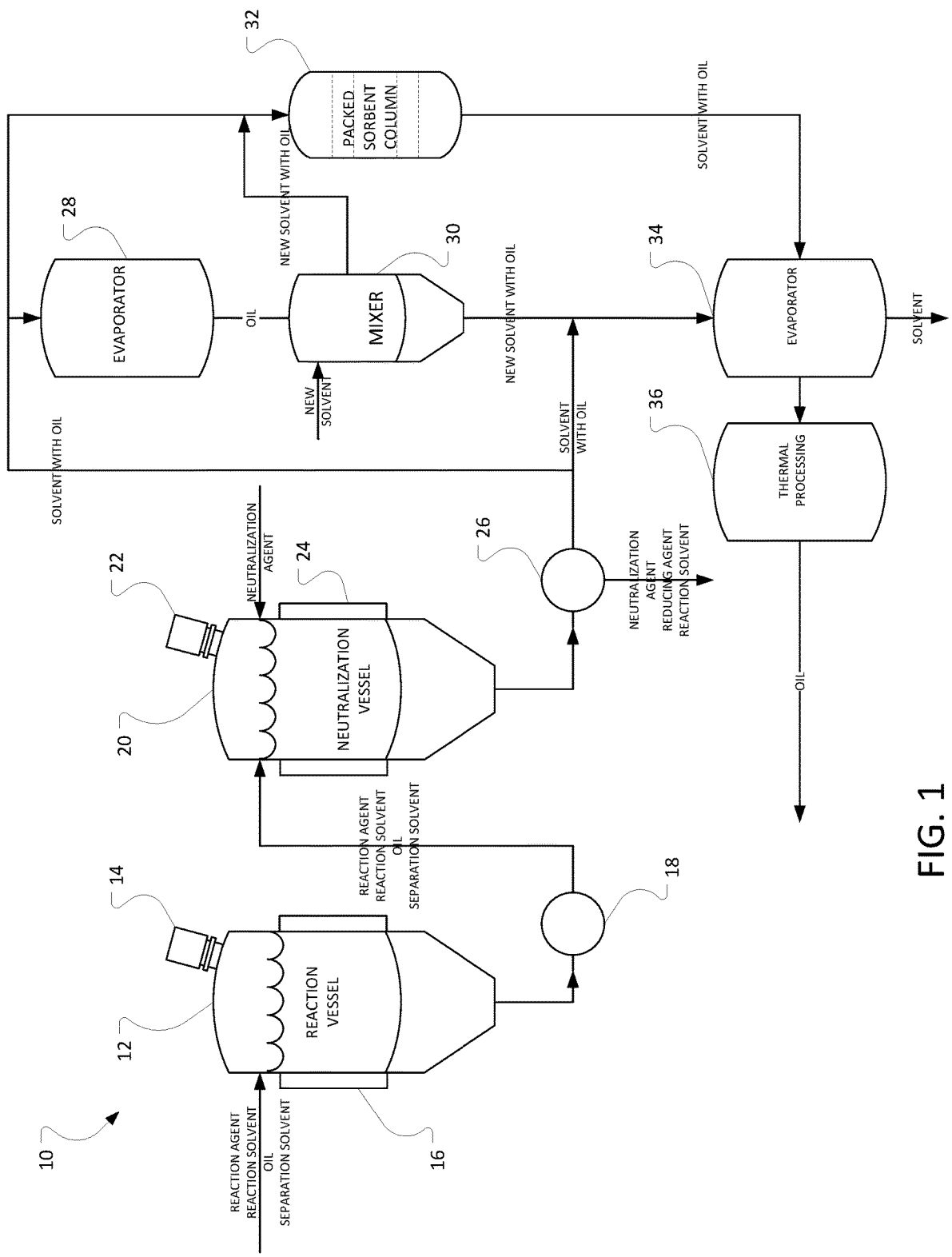
FIG. 1 shows an embodiment of a system for the remediation of pesticides from agricultural oils.

The embodiments here remove impurities from oils, including those oils containing either or both THC (tetrahydrocannabinol) or CBD (cannabidiol). The embodiments may apply to any agricultural oil. The term "agricultural oil" as used here means any oils and extracts derived from plants including hops bittering extracts, edible oils, fruit extracts used in brandy and other alcoholic drinks, essential oil extracts, edible oils, and oils and other substances used in vaporizing cigarettes or devices (vaping). Plant extracts of any type in the below discussion are included in the term "oils."

While the discussion below focuses on the remediation of pesticides in oils derived from hemp and *cannabis*, no limitation to those particular oils is intended, nor should any be implied. Other types of oils may not have as stringent requirements as *cannabis* and hemp but may still benefit from the remediation of the pesticide content for purity and/or product liability concerns.

To simplify the below discussion, it will use the term "*cannabis*" to apply to both *cannabis* and hemp. Industrial hemp is also a *cannabis* plant, but under the 2018 Farm Bill the term "industrial hemp" applies to those plants that contain less than 0.3% THC. However, it is still a *cannabis* plant, so the use of the term "*cannabis*" will apply to any variety of *cannabis*, regardless of THC or CBD content.

The term "remediation" will include both neutralization, in which a harmful pesticide or pesticide component is rendered biologically inactive, and removal, in which the pesticide or pesticide component is removed from the oil. Removal may mean complete removal or removal to a level that is below the maximum allowable concentration of that component, such as below 0.1 PPM.

The embodiments here may remediate many different types of pesticides. The inventors have gathered data from a number of independent, third-party laboratories and created a list of the most commonly detected and problematic pesticides present in *cannabis* oils. The below list is of these pesticides in alphabetical order. The embodiments here remediate all of these pesticides as well as others not listed. The list includes: abamectin; acephate; acequinocyl; azoxystrobin; bifenazate; bifenthrin; boscalid; captan; carbaryl; carbofuran; chlorantraniliprole; chlorfenapyr; chlorpyrifos; cyfluthrin; cypermethrin; daminozide; DDVP; diazinon; ethoprophos; etofenprox; etoxazole; fenoxycarb; fenpyroximate; fipronil; imazalil; imidacloprid; malathion; metalaxyl; MGK-264; myclobutanil; paclobutrazol; permethrins; piperonyl butoxide; prallethrin; propiconazole; pyrethrins-I and -II; pyridaben; spinosad-D and -A; spiromesifen; spirotetramat; tebucanazole; and trifloxystrobin.

Organic chemistry is largely driven by functional group characterization. A functional group is portion of a molecule that is recognized and characterized by a particular group & configuration of bound atoms. These functional groups (or absence of functional groups) define how the molecule will interact with other molecules. Molecules with the same functional groups interact in similar manners. In organic chemistry, molecules are often comprised of a carbon backbone with functional groups attached to it.

The vast majority of the contaminants, such as from the pesticides listed above, fell into the following categories: esters, organophosphates, nitriles, carbamates, or carbonates.

By organizing the impurities by reactive group it was determined that they could be altered and/or decomposed in a manner that would render them no longer biologically active and therefore harmless, or that would facilitate their removal.

Tetrahydrocannabinol (THC) or Cannabidiol (CBD) extracts are composed largely of either CBD or THC.

Tetrahydrocannabinolic Acid (THCa) is naturally produced in *Cannabis Sativa* and *Cannabis* Indica plants. THCa naturally undergoes decarboxylation to form THC, the psychoactive component that give marijuana its effects. THCa decarboxylates at room temperature to THC slowly, or at elevated temperature very rapidly. This method has been developed to decontaminate THC oil, because it is the predominant form of THC, but is not intended to exclude THCa purification from this method's scope.

Similarly, Cannabidiolic Acid (CBDa) is produced as the natural precursor to CBD in *Cannabis Sativa* and *Cannabis*

Indica plants. CBDa also naturally decarboxylated into CBD. This study is concerned with decontaminating CBD oil for the same reason mentioned in 0017. Both THC and CBD have very similar molecular structures, and thus are purified effectively by the same procedure. This method has been developed to also decontaminate both CBD oil and THC oil.

Both THC and CBD are relatively stable molecules not prone to rapid hydrolysis in acidic or alkaline conditions. They are also not subject to modification by weak or strong reducing agents.

these impurities render many of them no longer biologically active and therefore harmless to human and other animals. The methodology also has the added benefit of rendering all of the modified and/or decomposed compounds easier to remove via normal phase chromatography.

The modification and/or decomposition of these impurities in all cases facilitates and improves separation of the impurity from THC and CBD. The reacted products of the impurities are all more polar than the original impurities, and thus have increased retention time during normal phase chromatography. Further, the reacted products of the impu-

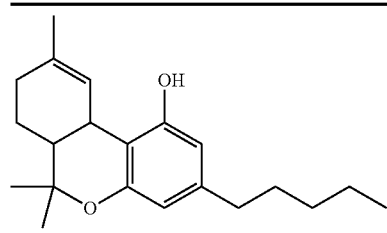

THC
(-)Δ⁹-trans-tetrahydrocannabinol

| | |
|---|---|
| CAS: | 1972-08-3 |
| Formula: | $C_{11}H_{30}O_2$ |
| Molecular Weight: | 314.46 g/mol |
| Major Isotopic Mass: | 314.2246 g/mol |
| Melting Point: | viscous oil (not crystalline) |
| pKa: | 10.6 |
| log P: | 6.99 (octanol/water) |
| Solubilities: | |
| Water: | insoluble (2.8 mg/2.8 mg/L @ 23° C.) |
| Ethanol: | soluble |
| Chloroform: | soluble |
| Hexane: | soluble |
| Pharmacological Characteristics: | |
| Euphoriant | Anti-inflammatory |
| Analgesic | Anti-emetic |

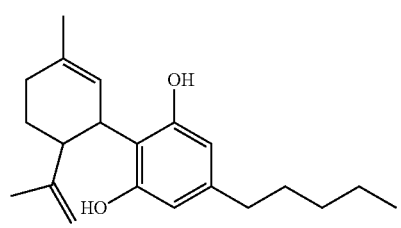

CBD
Cannabidiol

| | |
|---|---|
| CAS: | 23978-85-0 |
| Formula: | $C_{22}H_{30}O_4$ |
| Molecular Weight: | 314.46 g/mol |
| Major Isotopic Mass: | 314.2246 g/mol |
| Melting Point: | 66-67° C. |
| log P: | 5.79 (octanol/water) |
| Solubilities: | |
| Water: | insoluble |
| Ethanol: | soluble |
| Chloroform: | soluble |
| Hexane: | soluble |
| Pharmacological Characteristics: | |
| Anti bacterial | |
| Antibiotic | |

The THC and CBD oil can be purified on silica using a standard phase chromatography technique to remove a limited number of the impurities. Standard phase chromatography is an established technique for the separation of different molecules. A mixture of compounds including a target compound A are dissolved in an organic solvent mobile phase and flowed over a bed of silica. Each compound in the mixture will have a slightly different affinity for the silica versus the mobile phase and therefore a slightly different migration rate & retention time in the silica bed. Compound A can be collected separately from the others in the mixture at the end of the bed, thereby purification of Compound A can be achieved.

The limitation with using this method to effectively remove the impurities listed above is that many of those common impurities are very hydrophobic, just like THC & CBD, and therefore have similar retention times during standard phase and reverse phase chromatography, which results in poor separation of the impurities from the THC and CBD oil. Performing the separation of all of these compounds via standard or reverse phase chromatography is minimally successful and cost prohibitive, therefore an improved technique for removing these impurities is required.

The methodology laid forth in this document modifies and/or decomposes many of these impurities. The changes to rities are in some cases so polar that they become substantially water soluble, and can be separated from the THC or CBD oil via aqueous/organic liquid-liquid extractions. THC and CBD are both insoluble in water.

Analysis of the functional groups of the pesticides revealed that the majority of the common pesticides could be altered via reduction, alkaline hydrolysis, or acidic hydrolysis. The products of these reactions are all easier to separate from the THC or CBD in the oil than the original pesticide via liquid-liquid extraction or cleanup on silica. The following reactions were predicted, tested, and confirmed for the pesticide contaminants listed above.

Esters can be decomposed into two separate alcohols by reduction with a strong reducing agent.

General Reduction Reaction

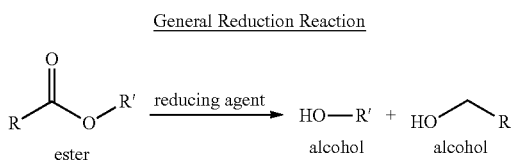

A strong reducing agent, such Lithium Aluminum Hydride (LAH) cleaves an ester into two corresponding alcohols as shown above. Alcohols are much more polar than esters, and thus have increased retention time on normal phase chromatography. This increase in retention time should facilitate better separation between CBD or THC and the alcohol decomposition products. The resulting alcohol product molecules will also be more water soluble than the original ester, thus making it potentially possible to separate the alcohol decomposition products from THC or CBD via a simple aqueous/organic liquid-liquid extraction.

An example of the reductive decomposition of Pyrethin II with Lithium Aluminum Hydride is shown below. There are three reaction products in this case, one of which is methanol. Both of the ester functional groups (shown in red in Pyrethrin II) are split into their corresponding alcohol decomposition products. The ketone functional group shown on the left is also reduced by LAH to a hydroxyl group.

cantly increased retention time in normal phase chromatography over the original molecule.

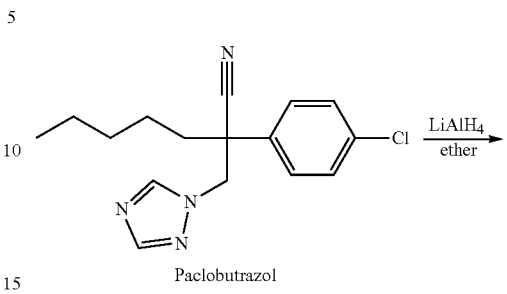

Paclobutrazol

Example Reduction Reaction

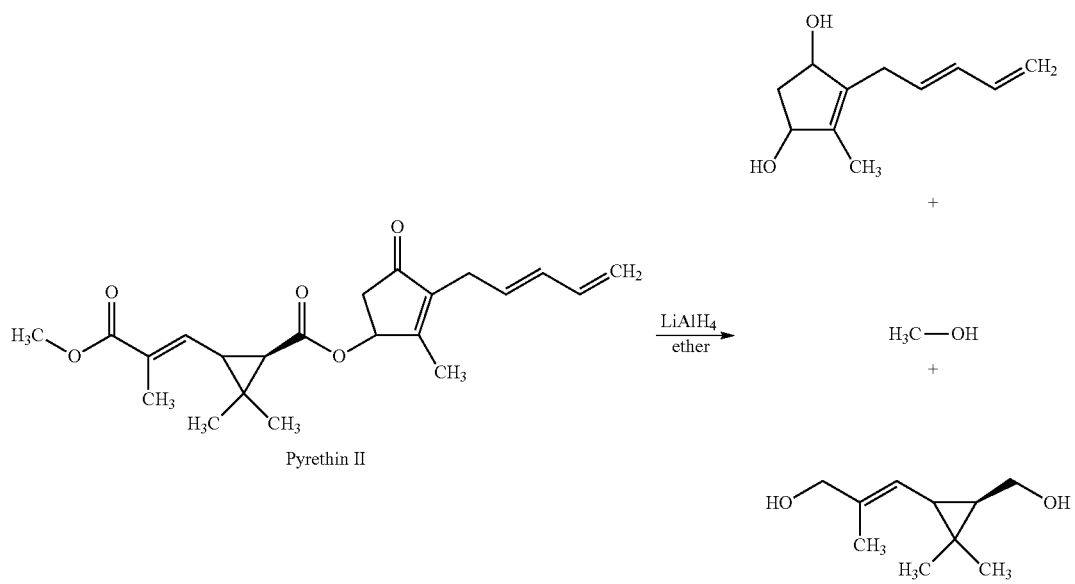

Pyrethin II

Regarding nitriles, a strong reducing agent, such as LAH mentioned above, reduces them into the corresponding amines as shown below.

General Nitrile Reduction Reaction

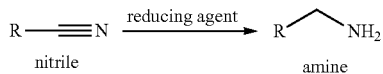

Amines are much more polar than nitriles, and thus have increased retention time on normal phase chromatography. This increase in retention time should facilitate better separation between CBD or THC and the amine reaction product. The resulting amine product molecules will also be more water soluble than the original nitrile, thus making it potentially possible to separate the amine reaction product from THC or CBD via a simple aqueous/organic liquid liquid extraction.

An example of the reduction of Paclobutrazol with Lithium Aluminum Hydride in an ether is shown below. The reaction product is a primary amine, which shows a signifi- Organophosphates are generally readily hydrolyzed in both strongly acidic or basic conditions. When conducting a reduction using LAH in THF, it is necessary to neutralize the excess LAH at the end of the reaction with either a simple alcohol or water. By neutralizing with acidified water, the procedure described in this study subjects the reaction mixture to both alkaline and acidic conditions. Water is initially added slowly to react the remaining LAH remaining in the reaction mixture. The pH raises and the environment is alkaline. Then as additional acidified water is added to the mixture, the pH drops and the mixture is exposed to acidic conditions. The concentration, proportion, and timescale for adding the water and acidified water components can be varied in order to promote the complete hydrolysis of the organophosphate pesticides.

Hydrolyzed organophosphates are both water soluble and highly polar. They are easily separated from the reaction mixture via aqueous/organic liquid-liquid separations or normal phase chromatography.

Examples of organophosphate pesticides include:

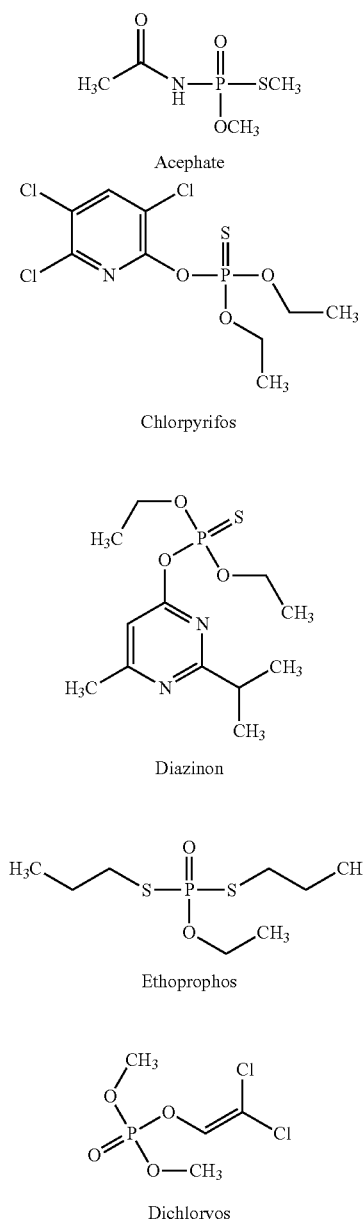

Acephate

Chlorpyrifos

Diazinon

Ethoprophos

Dichlorvos

Carbamates and carbonates can be hydrolyzed in strongly acidic conditions. Neutralizing the LAH reaction with acidified water hydrolyzes these pesticides. The hydrolysis decomposition products of carbamates and carbonates are more polar than the original molecules, and thus are more easily separated via aqueous/organic liquid-liquid extraction or purification on silica. Examples of the common carbamate/carbonate pesticides are shown below:

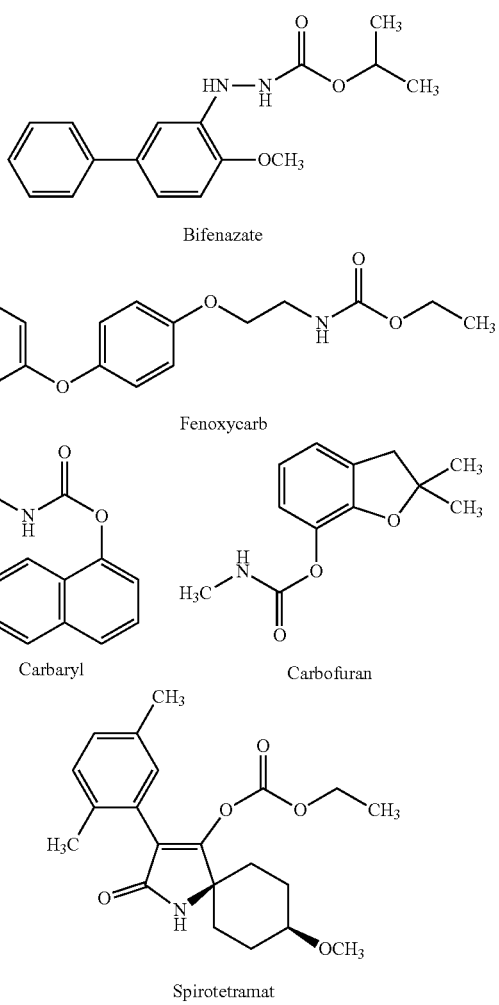

Bifenazate

Fenoxycarb

Carbaryl

Carbofuran

Spirotetramat

Generally, the embodiments here remove many of the common pesticide impurities from agricultural oils. The oil undergoes reduction with a reducing agent that produces a reaction mixture. The reaction mixture then undergoes a neutralization and extraction of the oils in a liquid/liquid extraction with acidified water. While these two processes will sufficiently remediate the pesticides for most uses, one could further purify the oils by performing purification on silica using normal phase or reverse phase chromatography and then performing thermal processing.

Figure 2:
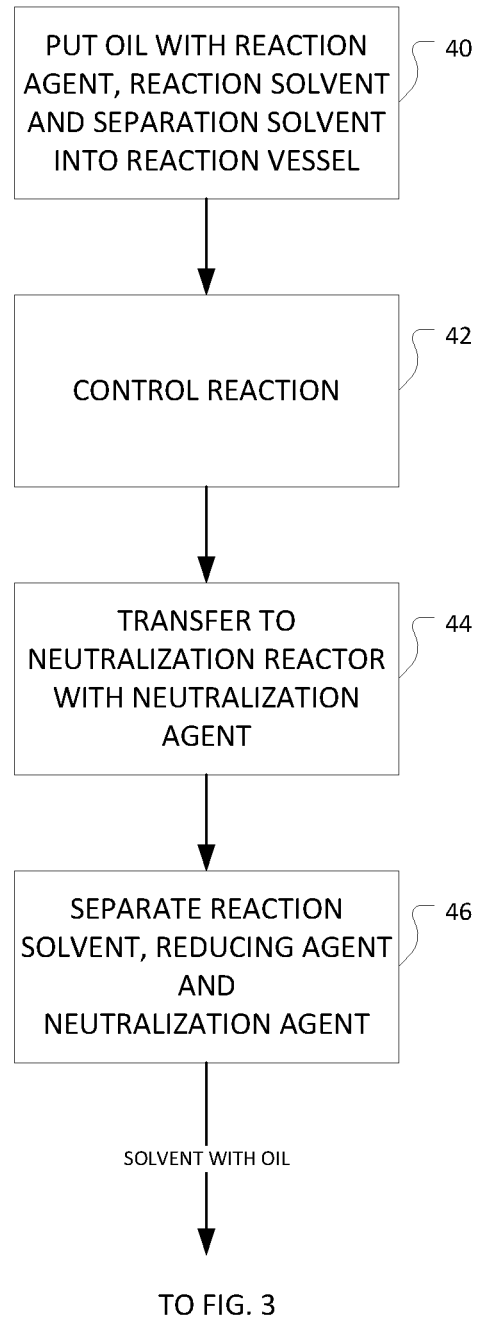
FIG. 2 shows a flowchart of an embodiment of a method for the remediation of pesticides from agricultural oils.

FIG. 1 shows an embodiment of a remediation apparatus or system 10 and FIG. 2 shows a flowchart of an embodiment of a method to remediate pesticides from agricultural oils. These two figures will be discussed simultaneously. In FIG. 2, the process starts with putting the agricultural oil with a reaction agent, a reaction solvent and a separation solvent into a reaction vessel such as the reaction vessel 12. One should note that the process may include mixing these substances together in the reaction vessel, pre-mixing them, or a combination of both.

In one embodiment, the reaction solvent comprise one selected from the group consisting of: tetrahydrofuran; heptane; diethyl ether; and methyl tertiary-butyl ether.

In one embodiment, the reducing agent comprises one selected from the group consisting of: lithium aluminum hydride; sodium borohydride; lithium borohydride; sodium hydride; di-isobutyl aluminum hydride; and sodium bis(2-methoxyethoxy) aluminum hydride.

In one embodiment, the reaction vessel may be blanketed with an inert gas to mitigate fire or explosion risk.

The reaction vessel 12 may have an agitator 14, and may be connected to a pump 18. In some embodiments, the pump may comprise the agitator, acting to mix the substances in the various vessels rather than having a separate agitator.

Returning to FIG. 2, the process then controls the reaction in the reaction vessel. This may include controlling the temperature of the reaction, with temperature control unit 16. Controlling the temperature includes both adding and extracting heat from the process. It may involve holding the mixture at a predetermined temperature for a predetermined period of time, adjusting the temperature of the reaction mixture after that period of time, as well as other methods of controlling the temperature. This process produces a pre-neutralization mixture in the reaction vessel 12 of FIG. 1 to which a separation solvent is added resulting in the pre-neutralization mixture including a separation solvent.

Pump 18 of FIG. 1 then transfers the pre-neutralization mixture to a neutralization reactor, shown as process 44 in FIG. 2. The neutralization reactor 20 of FIG. 1 may also include an agitator 22 and have a connection to a pump 26. The neutralization reactor 20 may already contain, or have added to it, a neutralization agent. In either case, the neutralization reactor contains a neutralization agent.

In one embodiment, the neutralization agent comprises one of the group consisting of: acidified water; methanol; alcohol; water; and, or a solution of potassium sodium tartrate tetrahydrate.

Using an agitator, either the agitator 22, if used, or the pump 26, mixes the neutralization agent and the pre-neutralization mixture. After mixing, the new mixture is allowed to separate into an aqueous layer and a separation solvent layer. Alternatively, a centrifuge may be used to speed the separation of the aqueous layer and the separation solvent layer. In FIG. 2, the process drains the aqueous layer from the separation solvent layer to separate the reaction solvent, reducing agent and neutralization agent from the separation solvent layer. In FIG. 1, pump 26 drains the aqueous layer from the neutralization reactor leaving the separation solvent layer in the neutralization vessel.

The process up to this point may provide sufficiently remediated oils, requiring only the distillation of the separation solvent from the oil. In FIG. 1, the solvent with oil exits the pump 26 and moves to evaporator 34. Evaporator 34 then distills the separation solvent that resides in the separation solvent layer from the remediated agricultural oils. Additionally, the agricultural oils may be further purified by optional thermal processing such as distillation of the oil as shown at 36 in FIG. 1, in the same or a different apparatus.

"Thermal processing" as used here means any process in which the oil is heated under a vacuum. This may include high vacuum distillation of the oils, molecular distillation, deodorization and/or steam stripping.

Figure 3:
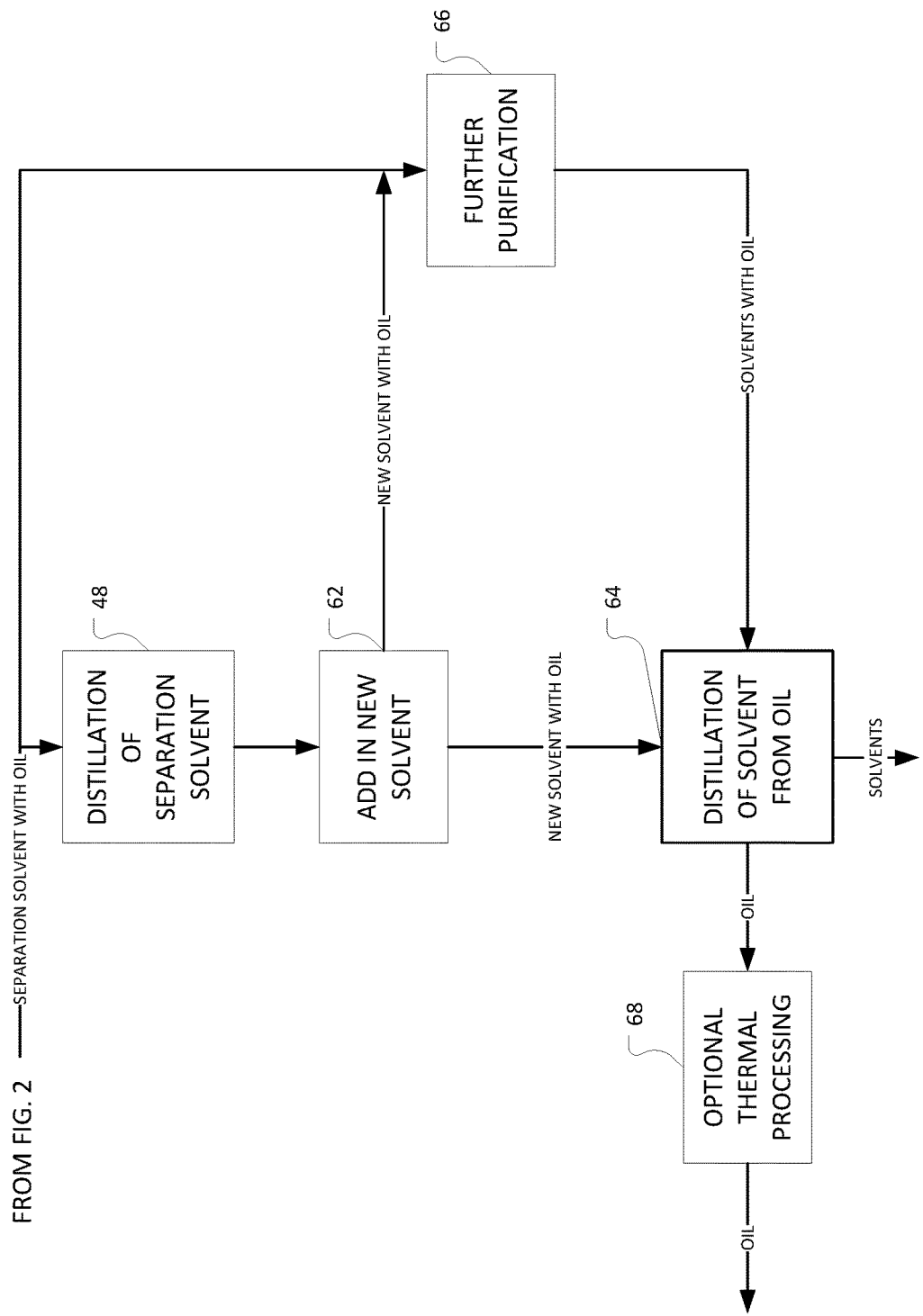
FIG. 3 shows a flowchart of an embodiment of a method of additional processing of remediated agricultural oils.

However, returning to FIG. 2, after the draining of the aqueous layer at 46, the solvent with oil may undergo further processing to produce purified, remediated, agricultural oils. FIG. 3 shows these additional processes as also discussed in FIG. 1.

In an embodiment, after the distillation of the solvent at 48 or in a different distillation path, a new solvent is added at 62. This may undergo further distillation at 64, resulting in purified, remediated, agricultural oils. These oils may undergo optional thermal processing at 68. In FIG. 1, the additional solvent path is shown where the solvent with oil from pump 26 travels to evaporator 28. Evaporator 28 removes the solvent from the oil and transfers the oil to a mixer 30. A new solvent is added at the mixer 30. This new mixture then moves to the evaporator 34 to continue the previous process, including the optional thermal processing unit 36. This results in purified, remediated agricultural oils mentioned above.

In another embodiment, the oil mixed with the new solvent exits mixer 30 and goes through additional purification, shown as 66 in FIG. 3. This further purification may also act on the separation solvent with oil from FIG. 2. In an embodiment, shown in FIG. 1 without limitation, the solvent with oil or new solvent with oil may pass through a packed sorbent column 32. Alternatively, the process may employ standard or reverse phase chromatography using a mobile phase. These would then pass to the evaporator 34.

In one embodiment, the mobile phase comprises one of the group consisting of: ethyl acetate and alkane; methyl tertiary-butyl ether and alkane; diethyl ether and alkane; dichloromethane and alkane; dichloromethane and methanol; toluene; tetrahydrofuran, or any combination thereof.

In an embodiment, the further purification may include additional purification processes after the sorbent column or chromatography processes. These may include any of the optional thermal processes mentioned above.

Example 1

The following example is broken into the steps mentioned above of: reduction; neutralization; purification; and thermal processing.

Reduction

Heat anhydrous THF to 25 C in a sealed and vented SS304 or SS316 reactor that is continually agitated. Optionally, the reactor can be blanketed with Nitrogen to mitigate any fire or explosion risk. Add a concentrated solution of 1 M LAH in THF to the THF that is already heated to 25 C. Minimal reaction should be observed. Ensure that the overall solution is approximately 25 C in temperature. The resulting THF solution should contain a concentration of approximately 0.22 M LAH. Slowly add the CBD or THC extract over a period of between 5 and 10 minutes. Vigorous reaction will be observed as the extract is slowly added to the solution. The reaction mixture should rise in temperature during this addition. Ensure that over the course of the addition the temperature increases in a controlled manner up to 55 C, but no higher or lower. Once all the extract is added to the reaction mixture, start a timer and allow the reaction to proceed for 60 minutes. Continue maintaining the temperature of the reaction at 55 C for the duration of the procedure, and ensure that agitation is constant throughout the reaction duration. At the end of 60 minutes, proceed to neutralization.

The ratio for ingredients in this example is: 1 Kg THC or CBD extract; 1222 g 1 M LAH in THF; 3245 g Anhydrous THF; 10200 g Heptane 27 Liters 0.125 M HCl/water solution for wash #1; 20 Liters of 0.125 M HCl/water solution for wash #2; 20 liters RO water for wash #3.

Other variations for the reduction exist. These include using different extract to THF to LAH to other ingredient ratios, and using other reducing agents such as Sodium Borohydride, Lithium Borohydride, Sodium Hydride, Dibal, Red-Al, or numerous others. One could reduce agitation, or use pumpover mixing instead. One could conduct the reaction in a different solvent such as heptane, diethyl ether, or MTBE, add reagents in different orders, and conduct the reaction at a different temperature or for a different duration.

Stop the heat flow into the reactor and immediately add the heptane at 20 C to the reaction mixture. The reaction mixture should cool to approximately 30 C with the addition of the heptane. Let this stir in the reactor for 5 minutes to ensure that the THF and the heptane are completely and thoroughly mixed. Once the 5 minutes is up, begin feeding the solution into a neutralization reactor as is described below.

Neutralization

The neutralization reactor contains the 0.125 M HCl & water solution. The neutralization reactor is held at 50 C. The reactor is vigorously agitated and turned over from top to bottom every few seconds. The reaction mixture is fed into this acid bath steadily and slowly over the course of approximately 5 minutes. Mix the solution vigorously for approximately 10 minutes after reaction mixture has been fully added to the acidic water solution. Stop mixing and allow the solution to stand until the heptane layer and the aqueous layer have fully separated. Drain the aqueous layer off the bottom and send this to solvent waste. Add an additional 20 Liters of acidified water to the heptane in the reactor, mix again for 10 minutes, and all the solution to separate again. Repeat this one more time with the RO water. The heptane layer now contains all of the THC or CBD extract, and the heptane can be distilled off to yield the CBD or THC oil again. As mentioned previously, this could be the end of the remediation process. For completeness, the remaining optional steps are included below.

Other variations for neutralization exist. One could Use a different solution to neutralize the reaction. One could use methanol or another alcohol, plain water, or a solution of Rochelle salts. One could add the solution into a smaller volume of plain RO water or water with a different buffer to increase the pH temporarily to allow the reaction mixture to become very alkaline before reducing the pH again. One could add the neutralization agent to the reaction mixture instead of adding the reaction mixture to the neutralization agent.

Purification

Optionally, the impurity reaction products can be removed from the CBD or THC oil. This is best achieved using bare silica and a mobile phase consisting of a non-polar mixture of solvents. The solvent mixture used is composed of EA/Heptane due to its low toxicity and good general performance. The CBD and THC have lower retention time than the impurity reaction products, and thus can be collected in the first fraction of solvent that passes through the packed silica bed. The CBD or THC extract should now be free of the majority of the common pesticide contaminants.

Other variations exist. One could purify the oil via reverse phase chromatography as well using C18 or a polymeric support as the stationary phase. One could purify the oil by using silica as a straight sorbent and passing the oil in concentrated form, or mixed in an alkane through the silica material. One could realize the separation using different combinations of mobile phases, such as MTBE/alkane, diethyl ether/alkane, DCM/alkane, DCM/methanol, toluene, THF, etc. . . . . Another variation would be to perform a further process using a different sorbent that could include, but are not limited to: silica, Florisil, polymeric resins, functionalized silicas, or other sorbents.

Thermal Processing

Optionally, the CBD or THC extract can be further purified following the previous purification. One could perform the purification by the thermal processes mentioned above, such as by distilling the CBD or THC rich oil under high vacuum. This is commonly done in the molecular distillation range using wiped film short path distillation equipment.

Other variations exist for the thermal processes, such as distillation with any type of high vacuum distillation equipment. One could use or not use a rectification column. One could perform multiple passes at higher and lower vacuum levels to remove material both more volatile and less volatile than the THC or CBD.

The inventors used this process on all forty-two of the commonly found pesticides as a sample. This procedure removed these impurities from THC or CBD oil when reduction was followed by both neutralization and purification. Just the reduction and neutralization process of this procedure removed or modified thirty-seven of the sample impurities.

This procedure was tested and confirmed to work for both THC and CBD oil with the 42 impurities listed herein. The procedure has much broader applicability and scope. This procedure could be used to remove a much broader set of pesticide or other classes of contaminants from THC or CBD oil. The procedure could also be used to remove this same broad set of impurities from hemp seed oil, edible oils in general, hops extract, or other concentrated extracts and essential oils.

This process may apply to products that have stringent pesticide control standards, or to products which the producers desire a higher level of quality and safety. No limitation to any type of agricultural product or the removal of any particular type of pesticide is intended nor should any be implied.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of remediating pesticides from an agricultural oil, comprising:
   mixing a reaction solvent, a reducing agent, and an agricultural oil into a reaction mixture in a reaction vessel;
   controlling the temperature of the reaction mixture;
   producing a pre-neutralization mixture including a separation solvent;
   transferring the pre-neutralization mixture into a neutralization reactor that contains a neutralization agent;
   mixing the pre-neutralization mixture with the neutralization agent and allowing separation into an aqueous layer and a separation solvent layer;
   draining the aqueous layer; and
   distilling the separation solvent in the separation solvent layer from the remediated agricultural oils.

2. The method as claimed in claim 1, further comprising agitating the vessel during predetermined period of time.

3. The method as claimed in claim 1, further comprising blanketing the reaction vessel with an inert gas to mitigate fire or explosion risk.

4. The method as claimed in claim 1, further comprising performing, at least once:
   mixing in additional neutralization agent after draining the aqueous layer and allowing repeated separation into aqueous and separation solvent layers;
   draining the aqueous layer to again produce the separation solvent layer;
   allowing separation into aqueous and separation solvent layers, wherein the distilling of the separation solvent is performed on the most recent separation solvent layer.

5. The method as claimed in claim 1, wherein controlling the reaction temperature includes maintaining a predetermined temperature for a predetermined period of time.

6. The method as claimed in claim 1, wherein controlling the reaction temperature includes adjusting the temperature of the reaction mixture.

7. The method as claimed in claim 1, wherein mixing the pre-neutralization mixture with the neutralization agent comprises mixing the pre-neutralization mixture with the neutralization agent, and then allowing separation by one of either letting the vessel stand unagitated while separation occurs or utilizing a centrifugal separator to increase the speed of separation.

8. The method as claimed in claim 1, wherein producing a pre-neutralization mixture including a separation solvent comprises one of either adding the separation solvent into the reaction mixture, or producing a pre-neutralization mixture from a reaction mixture that already contains separation solvent.

9. The method as claim in claim 8, wherein the separation solvent is the same as the reaction solvent.

10. The method as claimed in claim 1, further comprising further purifying the remediated agricultural oils to produce purified, remediated agricultural oils.

11. The method as claimed in claim 10, wherein further purifying the remediated agricultural oils comprises one of: performing standard or reverse phase chromatography, wherein the chromatography uses a mobile phase; passing the oil without solvents through at least one sorbent; and passing the oil with at least one solvent through sorbents.

12. The method as claimed in claim 11, wherein the mobile phase comprises one of the group consisting of: ethyl acetate and alkane; methyl tertiary-butyl ether and alkane; diethyl ether and alkane; dichloromethane and alkane; dichloromethane and methanol; toluene; tetrahydrofuran; or any combination thereof.

13. The method as claimed in claim 11, wherein the at least one solvent comprises at least one of the group consisting of: the separation solvent; a new solvent; and a mixture of the separation solvent and the new solvent.

14. The method as claimed in claim 1, wherein the reaction solvent comprises one selected from the group consisting of: tetrahydrofuran; heptane; diethyl ether; and methyl tertiary-butyl ether.

15. The method as claimed in claim 1, wherein the reducing agent comprises one selected from the group consisting of: lithium aluminum hydride; sodium borohydride; lithium borohydride; sodium hydride; di-isobutyl aluminum hydride; and sodium bis(2-methoxyethoxy) aluminum hydride.

16. The method as claimed in claim 1, wherein the neutralization agent comprises one of the group consisting of: acidified water; methanol; alcohol; water; and a solution of potassium sodium tartrate tetrahydrate.

17. The method as claimed in claim 10, further comprising additionally purifying the purified, remediated agricultural oils.

18. The method as claimed in claim 17, wherein additionally purifying purified, remediated agricultural oils comprises thermal processing.

19. The method as claimed in claim 18, wherein thermal processing comprises vacuum distillation using multiple distillate passes at higher and lower vacuums.

20. The method as claimed in claim 17, wherein additionally purifying the purified, remediate agricultural oils comprises separating one portion of the agricultural oil from the remaining agricultural oil by one or more distillations at specific absolute pressures and temperatures.

* * * * *